| United States Patent [19] | [11] Patent Number: 5,051,414 |
| Domaille et al. | [45] Date of Patent: Sep. 24, 1991 |

[54] INHIBITION OF HIV AND OTHER RETROVIRUSES BY POLYOXOANIONS

[75] Inventors: Peter J. Domaille, Coatesville, Pa.; John W. Blasecki, Newark, Del.

[73] Assignee: Dupont Merck Pharmaceutical Company, Wilmington, Del.

[21] Appl. No.: 389,030

[22] Filed: Aug. 3, 1989

[51] Int. Cl.$^5$ .................. A01N 55/02; A61K 31/555; C22C 14/00
[52] U.S. Cl. .................................... 514/184; 514/185; 420/417; 420/424; 420/430; 420/578; 420/580; 420/591
[58] Field of Search ............... 420/417, 424, 430, 578, 420/580, 591; 514/184, 185

[56] References Cited

FOREIGN PATENT DOCUMENTS 185-584  3/1984  Australia .
1575940 10/1980  United Kingdom .

OTHER PUBLICATIONS

Domaille et al., J. Am. Chem. Soc. 1986, 108, 2108–2109.
Altenau et al., Inorganic Chemistry, vol. 14, No. 2, 1975 pp. 417–421.
Domaille, J. Am. Chem. Soc. 1984, 106, 7677–7687.

*Primary Examiner*—Nathan M. Nutter

[57] ABSTRACT

There are disclosed pharmaceutical compositions containing polyoxoanions, methods of using them alone or in combination with other compounds, such as AZT and Poly-I:C for the treatment of retroviruses. Also disclosed are novel polyoxoanions.

6 Claims, No Drawings

INHIBITION OF HIV AND OTHER RETROVIRUSES BY POLYOXOANIONS

BACKGROUND OF THE INVENTION

1. Field of the Invention

This invention relates to pharmaceutical compositions containing polyoxoanions, methods of using them to treat retroviruses in a mammal, and to certain novel polyoxoanions.

2. Background Information

Antimony/tungsten heteropolyanion (HPA) compounds of the formula:

$$(NaSb_9W_{21}O_{86})^{18-}$$

pharmaceutical compositions thereof are described in EP 185584 wherein the alkali and/or alkaline earth and/or ammonium salt of the heteropolyanion are disclosed as being useful in the treatment of AIDS and similar syndromes. The mixed ammonium/sodium salts of the heteropolyanion of the formula set forth above, are generally referred to as HPA 23. FR 2245374 and FR 23343 disclose HPA 23 as being useful in treating viral infections responsible for sarcoma, leukemia, encephalomyocarditis and vesicular stomatitis.

BE 848836 describes the synergistic pharmaceutical combination of HPA23 or salts thereof and interferon as effective against leukemia and sarcoma viruses.

FR 2424028 discloses tungsten/arsenic heteropolyanions of the formula (1):

$$[As_4W_{40}O_{140}]^{-28} \quad (I)$$

and the salts thereof having the formula (II):

$$[M^{+x}(As^{+3})_4(W^{+6})_{40}(O^{-2})_{140}]^{-(28-x)}B_1^{+(28-x)} \quad (II)$$

wherein:

M ≧ 1 alkaline earth, transition (especially the first series) of Group IIIA, IVA, VA metal; the total charge, X, on M is >27;

B₁ is a monovalent alkali metal such as Na, K, Ba, Ag, Cu, Zn, Mn, Fe, Co or Ni.

The compounds of formula (II) are disclosed as having anti-viral activity and as being useful in human and veterinary medicine for controlling herpes, leukemia and sarcoma viruses.

BE 861233 discloses tungsten/antimony heteropolyanion compounds of the formula:

$$[MSb_9W_{21}O_{86}]^{-n}$$

wherein:

M is either absent or it represents an alkali or alkaline earth metal, other than sodium;

n is 19 when M is absent or n is 19—p, where p is the charge on the ion M;

which are useful for the treatment of leukemia and sarcoma viruses.

Japanese Patent 62 [1987]-230619 discloses alkalisalts of heteropolyacid ions, active against friend leukemia viruses, having the formula:

$$[XM_{12}O_{40}H_x]^{-p}$$

wherein:

X represents an element that becomes a cation, such as B, Al, Ga, In, Y, La, Ce, Pr, Nd, Sm, Eu, Gd, Ho, and Yb:

M is tungsten or molybdenum:

O is oxygen;

H is hydrogen:

x and p are positive integers with x being any of 1, 2, 6, 12 and 18.

Unlike the active compounds of the present invention, HPA 23, the most often cited heteropolyanion, has a total anion charge of $-18$, whereas the compounds active in the compositions disclosed herein each have a total anion charge of about $-5$ to $-12$, and preferably a total charge of about $-5$ to $-7$ per unit of dodecametalate framework.

Traditionally, as shown in the art, in order to change the overall charge of heteropolyanions, the central heteroatom has been changed. In the chemical compositions disclosed herein, the surface negative charge is increased by replacing tungsten cations with lower oxidation state metals such as vanadium (V($+4$ or $+5$)) or titanium (Ti($+4$)).

Many of the heteropolyanions known in the art are associated with serious side effects such as granulocytopenia and nephrotoxicity. In addition, very few of the known compounds are active against HIV or other retroviruses. Currently, only one drug Retrovir (AZT) is approved for treatment of HIV/AIDS. AZT is not a cure and in addition to serious side effects must be administered 4-6 times a day, and is very expensive. Given the worldwide scientific focus on AIDS and related syndromes, and the task of finding compounds useful in the treatment of these disease states as well as other retroviral diseases, there is a need for compounds with lower toxicity which are active against retroviruses, and particularly against HIV, and which can be dosed on a less frequent schedule.

SUMMARY OF THE INVENTION

According to the present invention there are provided pharmaceutical compositions which comprise a suitable pharmaceutical carrier and a retrovirus inhibiting amount of a polyoxoanion selected from the group consisting of: $K_6[BVW_{11}O_{40}]$, 1,2-$K_5[PV_2W_{10}O_{40}]$, $K_7[BV^{IV}W_{11}O_{40}]$, $\beta$-$Cs_5[PV_2W_{10}O_{40}]$, $K_6[SiTiW_{11}O_{40}]$, $K_7[PTi_2W_{10}O_{40}]$, $Na_{12}[P_2W_{15}O_{62}]$, and $K_9(NH_4)H_2[(OCe)_3(PW_9O_{34})_2]$.

Also provided are methods of treating retroviral infections in a mammal by administering to the mammal at least one of the aforesaid polyoxoanions either alone or in combination with Retrovir (AZT) or interferon or an interferon inducer.

Additionally provided are the novel polyoxoanions having the formulas:

$$\beta\text{-}Cs_5[PV_2W_{10}O_{40}]; \text{ and } K_6[SiTiW_{11}O_{40}].$$

DETAILED DESCRIPTION

The compounds useful in the present invention are
1. $K_6[BVW_{11}O_{40}]$
2. 1,2-$K_5[PV_2W_{10}O_{40}]$
3. $K_7[BV^{IV}W_{11}O_{40}]$
4. $\beta$-$Cs_5[PV_2W_{10}O_{40}]$
5. $K_6[SiTiW_{11}O_{40}]$
6. $K_7[PTi_2W_{10}O_{40}]$
7. $Na_{12}[P_2W_{15}O_{62}]$
8. $K_9(NH_4)H_2[(OCe)_3(PW_9O_{34})_2]$ They can be synthesized as described in the following publications: Domaille, P. J., *J. Amer. Chem. Soc.*, 104, 7677 (1984); Altenars, J. J., et al., *Inorg. Chem*, 14, 417 (1975); Domaille, P. J., *J. Amer. Chem. Soc.*, 108, 2108 (1986); Domaille, P. J., et al., Inorg. Chem., 22, 818 (1983); Contant, R., et al., *J. Chem. Res. Miniprint*, 2601 (1977); Contant R., et al., *J. Inorg. Nucl. Chem.*, 43, 1525 (1981): Knoth, W. H., et al., *Inorg Chem.* 25, 1577 (1986). The synthesis and properties of heteropolyanions in general are discussed in *Heteropoly and Isopoly Oxometalates*, M. T. Pope, (Springer-Verlag 1983).

The following examples describe the detailed synthesis of the eight compounds useful in the present invention. All parts and percentages are by weight unless otherwise indicated.

EXAMPLE 1

Preparation of $K_6[BVW_{11}O_{40}]$ (Compound 1)

Sodium tungstate dihydrate (36.3 g, 110 mmol) was dissolved in 60 mL of water and the pH was reduced to 6.3 by the addition of glacial acetic acid. Boric acid (25 g, 40 mmol) was added and the mixture was heated to about 80° C. Vanadyl sulfate (1.8 g, 11 mmol) in a minimum volume of water was added to the hot solution. The product was precipitated by addition of potassium chloride (20 g, 270 mmol) and subsequent cooling to 0° C. for about 30 minutes. The product was redissolved in 60 mL of water, the pH was adjusted to about 5.0 by the addition of acetic acid and the solution reheated to about 80° C. The hot solution was filtered to remove any insoluble impurity. The filtrate was cooled overnight to produce 20 g of dark-black needle-like crystals. The crystals were added to 50 mL of water and heated to about 50° C. Bromine was added dropwise until a yellow solution appeared. The hot solution was passed through an analytical filter aid and then reduced to cloud point by rotary evaporation. This was refrigerated at about 0° C. overnight to yield approximately 15 g $K_6[BVW_{11}O_{40}]$.

EXAMPLE 2

Preparation 1,2-$K_5[PV_2W_{10}O_{40}]x.H_2O$ $Na_8H[PW_9O_{34}]$ (30 g, 12.5 mmol) prepared by methods known in the literature such as described in *Inorg. Chem.* (1977), 16, 2916-2921, was added to 60 mL of about 20° C. water and was vigorously stirred to produce a white slurry. After about 1 minute a solution of 4.2 g of $VOSO_4$ (26 mmol) in 17 mL of water was added dropwise over a period of 10 minutes, and the reaction mixture was stirred for an additional 30 minutes at about 20° C. The temperature of the mixture was increased to about 60° C. for 1 hour and then $Br_2$ was added until a clear orange solution resulted. Solid KCl (25 g) was stirred in and the mixture was heated briefly to about 80° C. and then filtered while hot. Upon cooling the filtrate produced 28.3 g of crystalline orange product which $^{31}P$ NMR showed to be 85% of the 1,2-positional isomer. Recrystallization from 80° C., pH 2 water gave analytically pure material.

EXAMPLE 3

Preparation of $K_7[BV^{IV}W_{11}O_{40}]$

Sodium tungstate dihydrate (36.3 g, 110 mmol) was dissolved in 60 mL of water and the pH was reduced to 6.3 by addition of glacial acetic acid. Boric acid (2.5 g, 40 mmol) was added and the mixture heated to about 80° C. Vanadyl sulfate (1.9 g, 11 mmol) in a minimum volume of water was added to the hot solution. The product was precipitated by addition of potassium chloride and subsequent cooling to about 0° C. for 30 minutes. The product was redissolved in 60 mL of water, the pH adjusted to 5.0 by the addition of acetic acid and the solution was reheated to about 80° C. The hot solution was filtered to remove insoluble impurities. The filtrate was cooled overnight and produced 20 g of dark-black needle-like crystals of the subject material.

EXAMPLE 4

Preparation of $\beta$-$Cs_5[PV_2W_{10}O_4]$

Solid $Cs_7[PW_{10}O_{36}]$ [8.75 g, 2.6 mmol prepared as described in *J. Am. Chem. Soc.*, 1865, Vol. 103 (1981)], was slowly added to a solution of vanadyl sulfate (1.5 g, 9 mmol) in 50 mL of water. The solution was stirred for about 1 hour and approximately 12 g of black solid collected by filtration. The solid was redissolved in 200 mL of $H_2O$ and bromine was added dropwise until the solution turned orange. The solution was rotary evaporated until cloudiness developed and then chilled overnight at about 0° C. Filtration yielded 4.5 g of $\beta$-$Cs_5[PV_2W_{10}O_{40}]$. $^{51}V$ NMR, 30° C., pH 3.5: $-544.4(1)$, $-555.2(1)$, J=20 Hz. $^{183}W$ NMR: $-78.1(1)$, $-89.9(1)$, $-92.2(1)$, $-100.0(1)$, $-103.4(1)$, $-123.4(2)$, $-129.6(2)$, $-158.1(1)$.

EXAMPLE 5

Preparation of $K_6[SiTiW_{11}O_{40}]$

Titanium tetrachloride (2 mL, 18 mmol) was added dropwise with stirring to a 250 mL solution of $K_8[SiW_{11}O_{39}].xH_2O$ (25 g, 8 mmol) prepared as described in *J. Inorg. Nucl. Chem.* (1977), Vol 39,999. The mixture was refluxed for about 1 hour and passed through Celite ® analytical filter aid. The solution was reduced in volume to approximately 100 mL by vacuum evaporation and the pH increased to 5.0 with the dropwise addition of a saturated solution of potassium carbonate. The solution was heated to about 60° C. for 15 minutes and passed through Celite ® analytical filter aid. The solution volume was reduced by rotary evaporation until preparation was initiated. Chilling for 2 hours at about 0° C. yielded 12 g of $K_6[SiTiW_{11}O_{40}]$. $^{183}W$ NMR: $-106.5(2)$, $-107.4(2)$, $-109.6(1)$, $-119.4(2)$, $-132.1(2)$, $-133.8(2)$.

EXAMPLE 6

Preparation of $K_7[PTi_2W_{10}O_{40}].xH_2O$

Sodium dihydrogen phosphate (30 g, 215 mmol) was added to a solution of sodium tungstate dihydrate (150 g, 455 mmol) in 500 mL of water. Titanium tetrachloride (9 mL, 80 mmol) was added dropwise with stirring. The mixture was refluxed for about 1.5 hours, cooled to about 25° C., and passed through Celite ® analytical filter aid. Solid potassium chloride (150 g, 2 mmol) was added to the solution and stirred for about 2 hours. The solid was collected and recrystallized from water to obtain 80 g of $K_7[PTi_2W_{10}O_{40}]$.

EXAMPLE 7

Preparation of $Na_{12}[P_2W_{15}O_{62}]$

Sodium perchlorate (300 g, 2.4 mol) was added to a solution of $K_6[P_2W_{18}O_{62}]$ (400 g, 87 mmol) in water to eliminate the potassium ions. The solution was filtered and the filtrate adjusted to pH 9 by the addition of 1M sodium carbonate. A milky precipitate formed immediately and was difficult to filter. The product was best isolated by centrifuging, and decanting of the supernatant solution. The product was washed with 1M sodium chloride, ethanol, and finally, diethyl ether before being dried under a vacuum, to obtain 210 g of $Na_{12}[P_2W_{15}O_{62}]$.

EXAMPLE 8

Preparation of $K_9(NH_4)H_2[OCe)_3(PW_9O_{34})_2].4H_2O$

Ceric ammonium sulfate (24 g, 28 mmol) was added to a fresh slurry of $Na_8H[PW_9O_{34}]$ (60 g, 22 mol), prepared as described in *Inorg. Chem.* (1977), Vol 16, 2916, in water (400 mL). The mixture was stirred for about 3 minutes and filtered. Potassium chloride (40 g) was added to the filtrate to precipitate a yellow solid. The product was recrystallized from 100 mL of 75° C. water to obtain 27 g of yellow solid. The material was then refluxed for about 1 hour in water (35 mL) and cooled to crystallize 16 g of the captioned material as a yellow crystalline solid.

UTILITY

HIV Infectivity Assay in ATH8 Cells

ATH8 cells are grown in RPMI 1640, supplemented with a 4 mM L-glutamine, 15% heat-inactivated fetal calf serum, 50 units/ml of penicillin, 50 μgm/ml of streptomycin and 50 units/ml recombinant interleukin-2. The cells are treated with polybrene (2 μg/ml) for 30 minutes, collected by centrifugation and resuspended in freshly harvested medium containing HIV-IIIB. Following 60 minutes of adsorption, the virus-infected cells are pipetted into wells ($2 \times 10^4$ cells/well) of a 96-well microtiter plate. Test compounds, diluted to a desired concentration, are then added to the wells at 0.1 ml/well. AZT (3'-Azido-3'-deoxythymidine) at 0.1-0.01 μg/ml in RPMI is used as a positive control compound. Uninfected, untreated cells serve as normal cell controls, while uninfected, compound-treated cells serve as cytotoxicity controls. The cultures are incubated at 37° C. in an atmosphere of humidified 5% $CO_2$ in air. The appearance of the cell pellet is monitored for 10 days, and the protective effect of compounds on the integrity of the cell pellet is scored in comparison to controls. The concentrations of test compounds required to give 50% protection of cells from virus-induced cytopathogenesis ($IC_{50}$) are shown for several polyoxoanions in Table 1.

HIV Infectivity Assay in H9 Cells

H9 cells are cultured in RPMI 1640 supplemented with 15% heat-inactivated fetal calf serum, 4 mM L-glutamine, 2-mercaptoethanol ($5 \times 10^{-5}$M), penicillin (50 units/ml) and streptomycin (50 μgm/ml). A cell-free suspension of HIV-IIIB is added to wells (0.1 ml/well), followed by an equal volume of compound from 100-1 μg/ml in 2-fold dilutions, diluted in medium to 3 X final concentration. Finally, H9 cells ($10^6$/ml) are added to each well (0.1 ml/well). The multiplicity of infection is 0.01. Fresh medium containing 1 X compound is added to the wells at 1, 2, 3 and 5 days of culture and the volume of the cultures is increased to 5 mL by day 7. Cultures are split 1:3 and fresh medium containing 1 X compound is again added on days 8 and 9. Cultures are terminated at day 10, at which time cell counts are determined and the supernatant fluid assayed for precipitable reverse transcriptase activity, using $dT_{15}.rA_n$ as the primer template and $Mg^{++}$ as the divalent cation. Results are expressed as counts per minute (cpm) of methyl[$^3$H]deoxythymidine triphosphate (16-18 Ci/mmol) incorporated per 10 microliters of culture supernatant. Uninfected, untreated cultures serve as cell growth/viability controls, while infected, untreated cultures serve as controls for viral reverse transcriptase production. The concentrations (μg/ml) of test compounds required to reduce production of HIV reverse transcriptase by 50% ($IC_{50}$) are shown for several polyoxoanions in Table 1 as compared to ($IC_{50}$) for AZT.

XC Plaque Assay for Quantitation of Friend Leukemia Virus (FLV) In Vitro

SC cells, grown in Eagle's minimal essential medium supplemented with 5% fetal calf serum, 1% L-glutamine (25 mg/ml), penicillin (100 IU/ml) and kanamycin (25 μgm/mL) (EMEM), are seeded in 60 mm petri dishes in 5 ml volumes, at $2 \times 10^4$ cells/ml. After overnight culture at 37° C. in a humidified atmosphere containing 5% $CO_2$, the cells are washed with Hanks balanced salt amino ethyl cellulose (DEAE) dextran (0.25 μg/ml in HBSS). The cells are again washed and infected with one ml of FLV suspension at a concentration predetermined to give 50-100 plaques per culture plate. After 2 hours of adsorption of 37° C., test compounds at 0.1-10.0 μg/ml (1 ml) are added to the plates. AZT is used as a positive control compound. Uninfected, untreated cultures serve as cell growth controls, while infected, untreated cultures serve as virus replication controls. The plates are fed with 8 ml of fresh EMEM (containing no compound) at 48 hours post-infection. At 5 days post-infection all cultures are examined for inhibition of cell growth in order to eliminate any cytotoxic compounds. The remaining plates are irradiated (UV source such as American Ultraviolet Lamp #782L20) and overlayed with 5 ml of an XC cell suspension ($4 \times 10^5$/ml). Three days after irradiation the cultures are fixed with methanol, stained with hematoxylin, washed and dried and plaques counted. Plaque inhibition is determined as percent reduction from infected, untreated controls. The concentrations (μg/ml) of test compounds required to inhibit plaque formation by 50% ($IC_{50}$) are given for several polyoxoanions in Table 1.

Solenomegaly Assay for Quantitation of Friend Leukemia Virus (FLV) In Vivo

Female Balb/c mice are infected intraperitoneally with 0.2 ml of FLV suspension at a concentration predetermined to induce spleen weights of 1-2 grams in vehicle-treated control mice at 21 days post-infection. Beginning 24 hours post-infection, mice (10/group) are treated with 10-100 mg/kg of test compound in Sterile Normal Saline for injection (USP) as a carrier for either intraperitoneal, subcutaneous, intravenous or oral route administration. Treatment is given once a day, continuing through 7 days post-infection. AZT is used as a positive control compound. Uninfected, vehicle-treated mice serve as normal spleen controls, while virus-infected, vehicle-treated mice serve as infected spleen controls. At 21 days post-infection the mice are sacrificed and spleens are surgically excised and weighed. Results are expressed as Treated/Control (T/C), where control represents the mean spleen weight of FLV-infected, vehicle-treated mice and is arbitrarily set to 1.0. The doses of test compounds required to inhibit virus-induced splenomegaly by 50% (ED$_{50}$) are shown in Table 1 as compared to AZT the control compound.

Splenomegaly Assay For Quantitation of Rauscher Leukemia Virus (RLV) In Vivo

Female BALB/c mice are infected intraperitoneally with 0.1 ml of RLV suspension at a concentration predetermined to induced spleen weights of 0.6-1 gram in vehicle-treated control mice at 21 days post-infection. Beginning at 24 hours pre-infection, mice (10/group) are treated intraperitoneally with 10-100 mg/kg of test compound in Sterile Water for Irrigation (USP). Treatment is given once a day, continuing through 14 days post-infection. Ribavirin is used as a positive control compound. Uninfected, vehicle-treated mice serve as normal spleen controls, while infected, vehicle-treated mice serve as infected spleen controls. At 21 days post-infection the mice are sacrificed and spleens are surgically excised and weighed. Results are expressed as Treated/Control (T/C), where control represents the mean spleen weight of RLV-infected, vehicle-treated mice and is arbitrarily set to 1.0. The dose of test compounds required to inhibit virus-induced splenomegaly by 50% (ED50) are shown in Table 1.

TA8LE 1

| Compound No. | Anti-Retroviral Activity | | | | |
|---|---|---|---|---|---|
| | HIV Infectivity ATH8 IC$_{50}$ ($\mu$g/mL) | HIV Infectivity RT/H9 IC$_{50}$ ($\mu$g/mL) | FLV In Vitro IC$_{50}$ ($\mu$g/mL) | FLV In Vivo ED$_{50}$ (mg/kg) | RLV In Vivo ED$_{50}$ (mg/kg) |
| 1 | 1.0 | <10 | 1 | 10-20 | 10-20 |
| 2 | 1.0 | <10 | 2.5 | 10-20 | 15-20 |
| 3 | 1.5 | <10 | 0.1 | 7.5 | N.T. |
| 4 | 1.6 | <10 | 7 | 10-20 | N.T. |
| 5 | 3.2 | N.T. | 3 | 20 | N.T. |
| 6 | 5.6 | N.T. | 5 | IA | N.T. |
| 7 | 2.6 | N.T. | N.T. | >20 | N.T. |
| 8 | 1.0 | N.T. | 10 | 10-20 | N.T. |
| AZT | 0.005 | N.T. | 0.005 | 100 | N.T. |

N.T. = not tested
IA = Inactive

As seen from the data in Table 1, AZT is more potent in vitro than the polyoxoanions of the present invention. However, the compounds of this invention are about 5-10 X more potent than AZT on a mg/kg basis in vivo. Therefore the compounds of the present invention may be dosed in lower amounts, for example they may be dosed at a range of about 10-100 mg/kg and preferably about 10-20 mg/kg as compared to AZT which is dosed at 100 mg/kg (See Table 1, in vivo data). In addition, the compounds of the present invention can be administered less frequently. By administering lower doses, of the less toxic compounds less often, good anti-retroviral activity is maintained while the risk of side effects is reduced.

Additionally, the compounds of the present invention demonstrate a good correlation between HIV and FLV activity which is not demonstrated by compounds known in the art. And also, the compounds have been shown to be active against LPBM-5 and SIV (Compound 1 has an IC$_{50}$ against SIV of <1 $\mu$g/mL and an ED$_{50}$ against LPBM-5 in vivo of about 10-20 mg/kg). Such activity is not shown in the art for other compounds having activity against HIV.

Combination Therapy with AZT Against FLV-Induced Splenomegaly

Since AZT is currently approved for the clinical treatment of HIV/AIDS, a combination therapy of AZT and the compounds of the present invention for the treatment of retrovirus and, particularly HIV/AIDS, may be a favorable alternative treatment plan. In order to determine how effective the compounds would be if given together, the following study was done.

FLV-infected mice are treated with compound 1 (0.8-20 mg/kg), alone or in combination with AZT (8-200 mg/kg). Starting one day post-infection compounds are given once daily for seven days. Compound 1 is administered subcutaneously (sc) while AZT is administered intraperitoneally (ip) in order not to physically mix the compounds at the same site. The results are shown in Table 2.

TABLE 2

Compound 1/AZT Combination Therapy Against FLV-Induced Splenomegaly

| AZT days 1-7 mg/kg (ip) | Cpd 1 mg/kg (sc.) days 1-7 | | | |
|---|---|---|---|---|
| | 0 | 0.8 | 4.0 | 20.0 |
| 0 | 1.0 | 1.0 | 0.94 | 0.52 |
| 8 | 0.83 | 1.16 | 0.68 | 0.34 |
| 40 | 0.69 | 1.08 | 0.65 | 0.28 |
| 200 | 0.46 | 0.68 | 0.46 | 0.08 |

(T/C values shown)

The data shown in Table 2 indicate levels of compound 1 or AZT which when administered alone (compound 1 at 20 mg/kg and AZT, at 200 mg/kg) gave about 50 percent reduction in splenomegaly, induced more than 90 percent reduction when used together. These data although suggestive of an additive effect of the two compounds, are significant in terms of the utility of dosing these compounds together.

Alternate Dosing Regimen with Combination Therapy with AZT Against FLV-Induced Splenomegaly As shown by the data in Table 2, the compounds of this invention are effective anti-retroviral agents when given either alone or in combination with AZT, what is suggested by the data in Table 2 and further supported by the data in Table 3 is that by combining a normal oral AZT dosing regimen (200 mg q5h daily) with a normal dose of compound 1 (80 mg/kg) given as infrequently as once every two weeks, 80-98% reduction in splenomegaly is achieved, as compared to dosing with AZT alone (about a 30-50% reduction). The following test was done to determine alternate dosing regimens.

FLV-infected mice are treated with compound 1 (80 mg/kg, S.C.) on the days shown in Table 3 alone or in combination with AZT (12.5-200 mg/kg, ip) administered daily for 7 days. Results are shown in Table 3.

TABLE 3

Alternate Dosing Regimen for FLV-Induced Splenomegaly with Combination of AZT and 1

| AZT mg/kg (ip) daily × 7 days | Cpd 1 (80 mg/kg S.C.) | | | |
|---|---|---|---|---|
| | Control | 1 & 10d | 1 & 14d | 1 & 17d |
| 0 | 1 | 0.21 | 0.17 | 0.5 |
| 12.5 | 0.93 | 0.07 | 0.1 | 0.28 |
| 50 | 0.71 | 0.15 | 0.02 | 0.23 |

TABLE 3-continued

Alternate Dosing Regimen for
FLV-Induced Splenomegaly with
Combination of AZT and 1

| AZT mg/kg (ip) | Cpd 1 (80 mg/kg S.C.) | | | |
|---|---|---|---|---|
| daily × 7 days | Control | 1 & 10d | 1 & 14d | 1 & 17d |
| 200 | 0.45 | 0.1 | 0.24 | 0.19 |

(T/C values shown)

The data shown in Table 3 indicate not only that two doses of compound 1 administered alone at intervals ranging from 10-17 days apart were efficacious, but also that compound 1 (80 mg/kg) given in two doses, two weeks apart, along with seven daily doses of AZT (50 mg/kg) resulted in 98% reduction of FLV-induced splenomegaly. This alternate dosing regimen provides for reduced doses of compound as well as less frequent administration which ultimately may result in fewer side effects, or reversal of some side effects seen with the compounds. Additionally, the combination demonstrated excellent anti-FLV activity, and the data suggests that the efficacy/toxicity of these compounds in vivo may be altered significantly by careful manipulation of dose levels and administration intervals.

In addition, the compounds of this invention may be useful in combination therapy with interferon or an interferon inducer such as PolyInosinic-PolyCytidylic Acid (Poly-I:C).

FLV-infected mice are treated with compound 1 (1.25-20.00 mg/kg S.C. daily×7d beginning one day post-infection alone or in combination with Poly-I:C (0.31-5.0 mg/kg ip daily×7d beginning one day post-infection. Results are shown in Table 4.

TABLE 4

Compound 1/Poly-I:C Combination
Therapy Against FLV-Induced Splenomegaly

| Poly-I:C mg/kg | Cpd 1 mg/kg S.C., daily × 7 days | | | |
|---|---|---|---|---|
| daily × 7d (ip) | 0 | 1.25 | 5.0 | 20.0 |
| 0 | 1.0 | 0.8 | 0.58 | 0.33 |
| 0.31 | 1.2 | 1.3 | 0.91 | 0.35 |
| 1.25 | 1.1 | 0.89 | 0.63 | 0.18 |
| 5.0 | 0.39 | 0.82 | 0.25 | 0.04 |

(T/C values shown)

As shown by the data, the combined dosing of these compounds at 20 mg/kg compound 1 and 5.0 mg/kg Poly-I:C resulted in 96% reduction of splenomegaly whereas individual dosing at these levels (compound 1 20 mg/kg and Poly-1:C 5 mg/kg) showed a 60% reduction. Again reduced doses with infrequent administration may result in equi-effective or greater anti-retroviral activity while reducing side effects.

DOSAGE AND DOSAGE FORMS

The heteropolyanions of this invention can be administered to treat retrovirus infections, including but not limited to HIV, SIV, FLV, RLV and LPBM-5. The compounds of this invention may also be useful against other (non-retroviral) infections.

A dose of about 10-100 mg/kg/day and preferably about 10-20 mg/kg/day (undivided) is effective against retrovirus-induced disease. The active ingredient can be administered parenterally (IP, IV, IM or SC) in solution in either sterile normal saline or sterile distilled water or orally in sterile normal saline or other suitable liquid dosage forms (elixir or syrup) or in solid dosage forms, such as tablets, enteric coated tablets or timed-release capsules. When these compounds are administered orally, a dose of 200-400 mg/kg/day is effective against retrovirus-induced disease.

Capsules

A large number of unit capsules are prepared by filling standard two-piece hard gelatin capsules each with about 100-250 mg of active ingredient incorporated into a suitable carrier coated to delay absorption.

Tablets

A large number of tablets are prepared by conventional procedures so that the dosage unit is 100-250 mg of active ingredient in a suitable carrier coated to delay absorption.

Solution

An aqueous solution is prepared for oral administration in sterile normal saline such that each ml contains about 5-10 mg of active ingredient. These solutions can contain coloring and/or flavoring to increase palatability.

Injectable

A parenteral composition suitable for administration by injection via the IP, IV, SQ or IM route is prepared by dissolving active ingredient in normal saline (USP) in a desirable concentration per mL or Sterile Water for Injection (USP) and sterilizing the solution by standard techniques. Additionally, excipients such as preservatives, stabilizers or buffers may be present.

What is claimed is:

1. A pharmaceutical composition comprising a suitable pharmaceutical carrier and a retrovirus inhibiting amount of a polyoxoanion selected from the group consisting of: $K_6[BVW_{11}O_{40}]$, $\beta\text{-}Cs_5[PV_2W_{10}O_{40}]$, $K_6[SiTiW_{11}O_{40}]$, $K_7[PTi_2W_{10}O_{40}]$, $Na_{12}[P_2W_{15}O_{62}]$, and $K_9(NH_4)H_2[(OCe)_3(PW_9O_{34})_2]$.

2. A pharmaceutical composition of claim 1 wherein the polyoxoanion is $K_6[BVW_{11}O_{40}]$.

3. A pharmaceutical composition of claim 1 wherein the polyoxoanion is $\beta\text{-}Cs_5[PV_2W_{10}O_{40}]$.

4. A pharmaceutical composition of claim 1 wherein the polyoxoanion is $K_6[SiTiW_{11}O_{40}]$.

5. A compound having the formula $\beta\text{-}Cs_5[PV_2W_{10}O_{40}]$ or a pharmaceutically acceptable salt thereof.

6. A compound having the formula $K_6[SiTiW_{11}O_{40}]$ or a pharmaceutically acceptable salt thereof.

* * * * *